United States Patent [19]

McKeown

[11] Patent Number: 4,613,433

[45] Date of Patent: Sep. 23, 1986

[54] ANAEROBIC FERMENTOR

[75] Inventor: Kevin J. McKeown, Windermere, England

[73] Assignee: Biomass Limited, England

[21] Appl. No.: 645,314

[22] PCT Filed: Dec. 20, 1983

[86] PCT No.: PCT/GB83/00348

§ 371 Date: Aug. 24, 1984

§ 102(e) Date: Aug. 24, 1984

[87] PCT Pub. No.: WO84/02518

PCT Pub. Date: Jul. 5, 1984

[30] Foreign Application Priority Data

Dec. 24, 1982 [GB] United Kingdom ............. 8236830

[51] Int. Cl.$^4$ .................... C02F 11/04; C12P 5/02
[52] U.S. Cl. .................... 210/150; 210/218; 210/261; 48/111; 435/311; 435/819; 435/801
[58] Field of Search .......... 210/150, 151, 261, 262, 210/283, 284, 603, 218, 180, 255, 617, 618; 48/111, 197 A; 435/167, 801, 819, 304, 311

[56] References Cited

U.S. PATENT DOCUMENTS

| Re. 27,721 | 8/1973 | Klock | 210/617 |
| 3,773,660 | 11/1973 | Hopwood | 210/617 |
| 4,248,972 | 2/1981 | Fischer et al. | 48/111 |
| 4,336,135 | 6/1982 | Price | 210/151 |

FOREIGN PATENT DOCUMENTS

| 2334107 | 1/1975 | Fed. Rep. of Germany | 210/617 |
| 31982 | 9/1964 | German Democratic Rep. | 210/261 |
| 627525 | 8/1949 | United Kingdom | 210/618 |

Primary Examiner—Benoit Castel
Attorney, Agent, or Firm—Leydig, Voit & Mayer, Ltd.

[57] ABSTRACT

An anaerobic fermentor comprising: a container vessel divided into at least two compartments each having a floor, a roof, and a layer of liquid-pervious packing material disposed horizontally across the compartment at a position intermediate the roof and the floor with its lower surface upwardly spaced from the floor and its upper surface downwardly spaced from the roof; liquid conduits connecting successive compartments in series and connecting the space between the roof and packing layer of one compartment to the space between the floor and packing layer of a succeeding compartment; means for introducing liquid to be treated to the first of the successive compartments; means for removing treated liquid from the last of the successive compartments; means for the removal of gas from the space between the packing layer and the roof of each compartment; and means for the removal of solids from the fermentor.

1 Claim, 2 Drawing Figures 4,613,433

ANAEROBIC FERMENTOR

BACKGROUND OF THE INVENTION

This invention is concerned with improvements in and relating to apparatus for the anaerobic fermentation of organic liquid materials or especially organic waste materials.

The anaerobic fermentation of organic waste materials is a well established process and has conventionally been carried out in a closed vessel which may be provided with stirring or agitation means. It has, further, been proposed to carry out anaerobic fermentation in a packed vessel, that is a vessel packed with an ordered or random array of packing elements such as are used in the chemical enginerring industry in, for example, distillation towers, scrubbers and the like.

SUMMARY OF THE INVENTION

It has now been found, in accordance with the present invention, that a layer of packing material may be used in an anaerobic fermentor not to serve as a medium in which anaerobic fermentation is carried but, rather, as a pervious barrier to define an anaerobic fermentation zone. By using such a layer of packing material it is possible to construct a reactor containing two or more anaerobic fermentation zones, thereby to provide a reactor capable of enhanced capacity.

According to the invention, therefore, there is provided an anaerobic fermentor comprising:

(i) a container vessel divided into at least two compartments each having a floor and a roof, a layer of liquid-pervious packing material disposed horizontally across the compartment at a position intermediate the roof and the floor with its lower surface upwardly spaced from the floor to define a fermentation zone therebetween and its upper surface downwardly spaced from the roof;

(ii) liquid conduits connecting successive compartments in series and connecting the space between the roof and packing layer of one compartment to the space between the floor and packing layer of a succeeding compartment;

(iii) means for introducing liquid to be treated into the space between the packing layer and the floor of the first of the successive compartments; and (iv) means for removing treated liquid from the space between the packing layer and roof of the last of the successive compartments.

In operation, the liquid to be treated is introduced, via the appropriate conduit, into the first compartment in the space between the floor and packing layer of that compartment (the fermentation zone). The liquid passes upwardly through the packing layer and is then conveyed, by the appropriate conduits, to the space between the floor and packing layer of the succeeding compartment and then flows upwardly through the packing layer of that compartment and is thence conveyed downwardly to the next successive compartment or, in the case of a two compartment reactor is discharged as treated liquid material.

Generally such compartment will be provided with means for discharging gas evolved during the anaerobic fermentation (typically methane) and such means will connect with the space intermediate the upper surface of the packing layer and the roof of the compartment. Further, one or more compartments may be provided with means for discharging solids (sludge) accumulating in the fermentation zone thereof.

The successive compartments of the fermentor in accordance with the invention may be arranged vertically or horizontally.

BRIEF DESCRIPTION OF THE DRAWINGS

In order that the invention may be well understood, reference will now be made to the accompanying schematic drawings in which.

DESCRIPTION OF THE PREFERRED EMBODIMENTS

Figure 1:
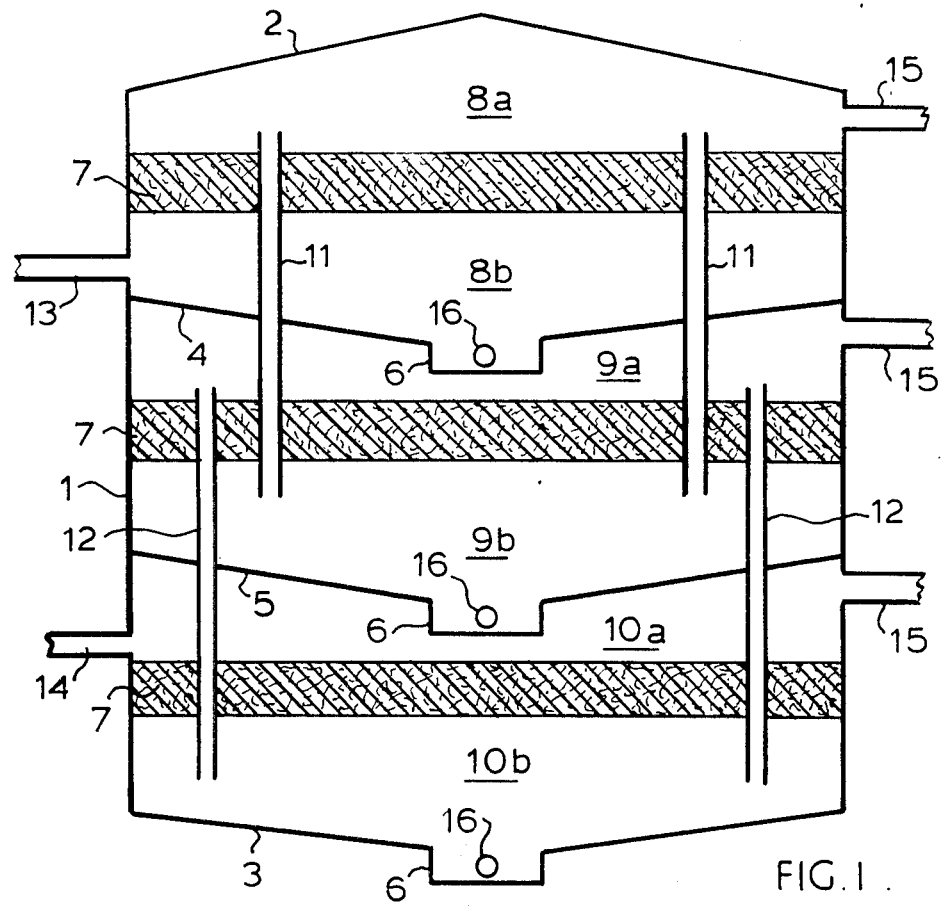
FIG. 1 is a vertical section through one embodiment of fermentor in accordance with the invention in which the compartments are arranged vertically.

As shown in FIG. 1 of the drawings, a reactor in accordance with the invention comprises a closed containing vessel comprising a generally cylindrical shell 1 having a roof 2 and a floor 3. The containing vessel is divided into three superimposed compartments by means of dividing members 4 and 5. Each of dividing members 4 and 5, and the floor 3 of the containing vessel are of generally downwardly dished shaped and each is provided at its centre with a sump 6. Each of the three compartments is provided with a layer of packing 7 extending horizontally across the compartment at a position between the roof and floor of the compartment and dividing each compartment into two zones, an upper zone (8a, 9a, 10a) between the upper surface of the layer of packing and the roof of the compartment and a lower zone (8b, 9b, 10b) between the lower surface of the packing layer and the floor of the compartment. Downwardly extending conduits 11 connected the upper zone 8a of the uppermost compartment with the lower zone 9b of the intermediate compartment and, similarly, vertically extending conduits 12 connect the upper zone 9a of the intermediate compartment with the lower zone 10b of the bottom compartment. A conduit 13, for the introduction of liquid to be treated, connects with the lower zone 8b of the upper compartment and a conduit 14, for the removal of treated liquid, connects with the upper zone 10a of the lower compartment.

Gas offtake conduits 15 connect with the upper zones 8a, 9a and 10a of the compartments at a position above the upper ends of conduits 11 and 12 (in the case of zones 8a and 9a respectively) and above the level of conduit 14 in the case of zone 10a. Each of sumps 6 is provided with a conduit 16 for removal of solids (sludge) accumulating therein.

In operation, liquid to be treated is introduced via conduit 13 into the lower zone 8b of the upper compartment, passes upwardly through the packing layer 7 in that compartment and thence downwardly through conduits 11 into the lower zone 9b of the intermediate compartment whence it flows upwardly through the packing layer 7 of that compartment and thence downwardly through conduits 12 into the lower zone 10b of the lower compartment and finally, having passed through packing layer 7 of that zone, is discharged via conduit 14. Gases evolved in the various compartments are taken off via conduits 15 and sludge accumulating in the bottom of the compartments may be discharged via conduits 16.

Figure 2:
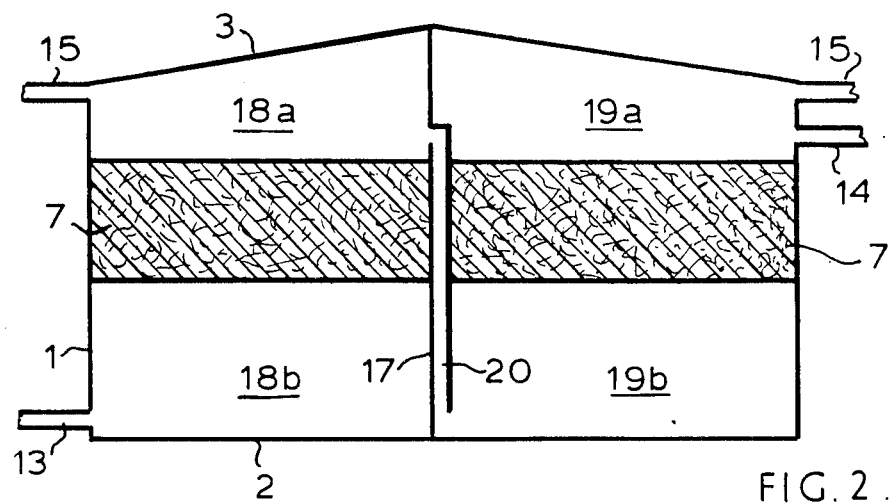
FIG. 2 is a vertical section through a fermentor in accordance with the invention in which the compartments are arranged horizontally.

The fermentor shown in FIG. 2 of the drawings comprises a containing vessel formed of a generally cylindrical shell 1 having a floor 2 and a roof 3. The interior of the containing vessel is divided into compartments by means of generally vertical divider 17 extending upwardly from floor 2 to roof 3 of the containing vessel.

Each of the components thus formed is provided with a generally horizontal packing layer 7 dividing the compartment into an upper zone (18a, 19a) and a lower zone (18b, 19b) in a manner similar to that described above in connection with the apparatus shown in FIG. 1. A generally vertical conduit 20 connects the upper zone, 18a, of the first compartment with the lower zone 19b of the second compartment. A conduit 13 for the introduction of liquid to be treated connects with the lower zone 18b of the first compartment and a conduit 14 for the discharge of treated liquid connects with the upper zone 19a of the second compartment. Each of the upper zones of the compartments is provided with a gas oftake conduit 15 located, in the case of the first compartment above the upper end of conduit 20 and, in the case of the second compartment, above liquid discharge conduit 14.

In operation, liquid to be treated is introduced via conduit 13 into the lower zone 18b of the first compartment and thence passes upwardly through the packing layer 7 of that compartment into the upper zone 18a and thence, via conduit 20, into the lower zone 19b of the second compartment and thence upwardly through the packing layer of that compartment into zone 19a and is finally discharged via conduit 14.

An important feature of the apparatus of the invention is, the provision of a layer of packing in each compartment. This packing may be formed of an ordered array of packing elements, e.g. perforated plates or vertical or sloped plates, but will more conveniently be formed of a dumped or random array of packing elements. So called "dumped" packings possess the advantage thay they may be simply introduced into the reaction vessel by being dumped therein. Suitable dumped packing elements include conventional Raschig rings, Pall-type rings and saddle-type packings. It has, however, been found that packing elements having an aspect ratio of less than unity (e.g. less than 0.66, preferably from 0.5 to 0.25) are of particular use in forming the packing array used in the apparatus of the invention. Suitable packing elements meeting the required aspect ratio criterion include rings which may or may not be provided with apertures in their side walls and internal radial or diametric rings, and so-called "Tellerette" rings (packing elements formed of a torroidal helix). As will be appreciated, such dumped packing elements should be supported on an appropriate perforated support. Random layers may also be formed of "demister" material, e.g. knitted of woven materails such as knitted or woven metal or plastics filaments.

The fermentation apparatus of the invention may be used to process a wide variety of organic waste liquids (by which term is meant aqueous solutions and/or suspensions of organic waste material) such as domestic sewage liquors, waste from food and beverage producing plants and from oil refineries.

The fermentation serves two principal functions namely (a) to reduce the BOD of the waste liquid whilst, (b) producing useful material such as methane from the waste material. Fermentation carried out in the fermentation apparatus of the invention may be carried out under conventional conditions for anaerobic fermentation that is at temperatures of from 20° to 80° C.

I claim:

1. An anaerobic fermentor comprising
   (i) a container vessel divided into at least two compartments each having a floor, a roof, and means for dividing the compartment into superposed zones and permitting upward fluid passage between the zones, said dividing and upward fluid passage means comprising a layer of liquid-pervious packing material disposed horizontally across the compartment at a position intermediate the roof and the floor with its lower surface upwardly spaced from the floor to define a fermentation zone therebetween and its upper surface downwardly spaced from the roof;
   (ii) liquid conduit means connecting successive compartments in series and providing downward liquid flow from the space between the roof and packing layer of one compartment to the space between the floor and packing layer of a succeeding compartment;
   (iii) means for introducing liquid to be treated into the space between the packing layer and the floor of the first of the successive compartments;
   (iv) means for removing treated liquid from the space between the packing layer and roof of the last of the successive compartments;
   (v) means provided in at least one fermentation zone for discharging solids from the fermentor; and
   (vi) means provided in each compartment between the upper surface of the packing layer and the roof of the compartment for discharging gas.

* * * * *